United States Patent [19]
Chang et al.

[11] Patent Number: 5,296,228
[45] Date of Patent: Mar. 22, 1994

[54] COMPOSITIONS FOR CONTROLLED DELIVERY OF PHARMACEUTICAL COMPOUNDS

[75] Inventors: Nienyuan J. Chang, Irvine, Calif.; Kenneth J. Himmelstein, Omaha, Nebr.

[73] Assignee: Allergan, Inc., Irvine, Calif.

[21] Appl. No.: 850,866

[22] Filed: Mar. 13, 1992

[51] Int. Cl.⁵ .................. A61K 9/10; A61K 47/36; A61K 47/34

[52] U.S. Cl. .................. 424/422; 424/423; 424/425; 424/427; 424/430; 424/433; 424/434; 424/435; 424/436; 424/486; 424/487; 424/488; 424/499; 514/944; 514/951; 514/781; 514/772.6

[58] Field of Search ............... 424/78.1, 78.12, 78.13, 424/78.04, 486–488, 501, 422–423, 425–428, 430, 434–436; 523/122; 564/944

[56] References Cited

U.S. PATENT DOCUMENTS

| | | | |
|---|---|---|---|
| 4,293,539 | 10/1981 | Ludwig et al. | 424/19 |
| 4,692,462 | 9/1987 | Banerjee | 424/78.12 |
| 4,795,644 | 1/1989 | Zentner | 424/468 |
| 4,814,183 | 3/1989 | Zentner | 424/485 |
| 4,859,461 | 8/1989 | Chow et al. | 424/79 |
| 4,911,920 | 3/1990 | Jani et al. | 424/78 |
| 4,940,588 | 7/1990 | Sparks et al. | 424/490 |
| 4,952,402 | 8/1990 | Sparks et al. | 424/419 |
| 4,983,392 | 1/1991 | Robinson | 424/427 |
| 4,996,047 | 2/1991 | Kelleher et al. | 424/79 |
| 5,071,646 | 12/1991 | Malkowska et al. | 424/497 |

FOREIGN PATENT DOCUMENTS

| | | | |
|---|---|---|---|
| 0254811 | 2/1988 | European Pat. Off. | B01J 39/04 |
| 0254822 | 2/1988 | European Pat. Off. | B01J 39/04 |
| 0429732 | 5/1991 | European Pat. Off. | A61K 9/06 |
| 89126026 | 3/1989 | Japan | A61K 9/00 |
| 9211871 | 7/1992 | PCT Int'l Appl. | A61K 47/48 |

*Primary Examiner*—Edward Webman
*Attorney, Agent, or Firm*—Poms, Smith, Lande & Rose

[57] ABSTRACT

Sustained release pharmaceutical compound delivery compositions and methods for their production are disclosed wherein ion exchange resin particles are loaded with releasably bound pharmaceutical compounds and incorporated in an aqueous reversibly gelling polymeric solution. The pores of the ion exchange resin are sufficiently small to lock in the pharmaceutical compound without exposure to the large polymer molecules. The pharmaceutical compound remains bound within the pores of the ion exchange resin particles until after administration to a target tissue site where small ions migrate into the pores and initiate an exchange reaction.

4 Claims, 1 Drawing Sheet

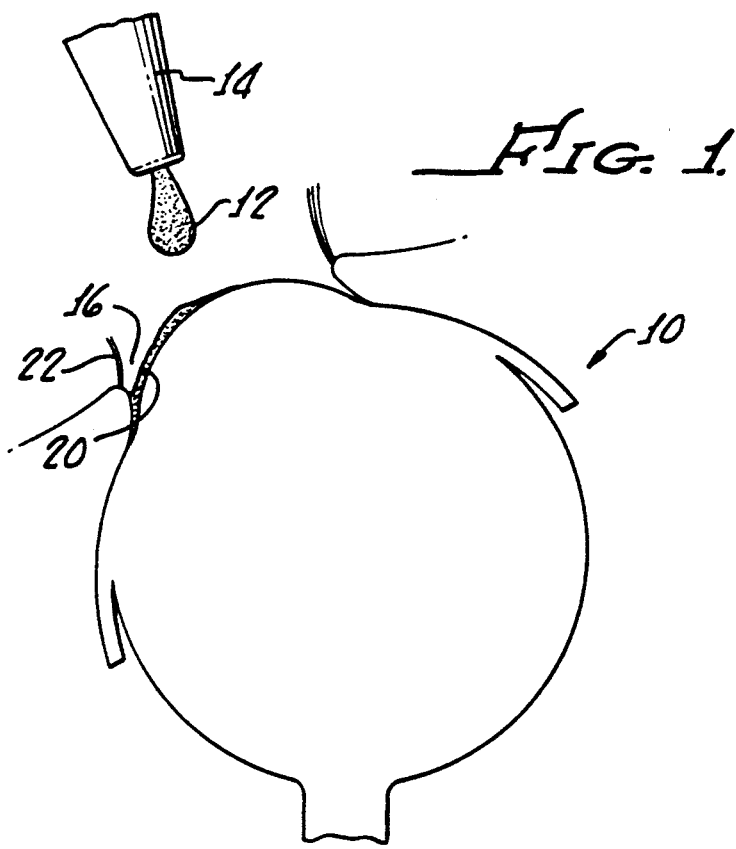
FIG. 1.
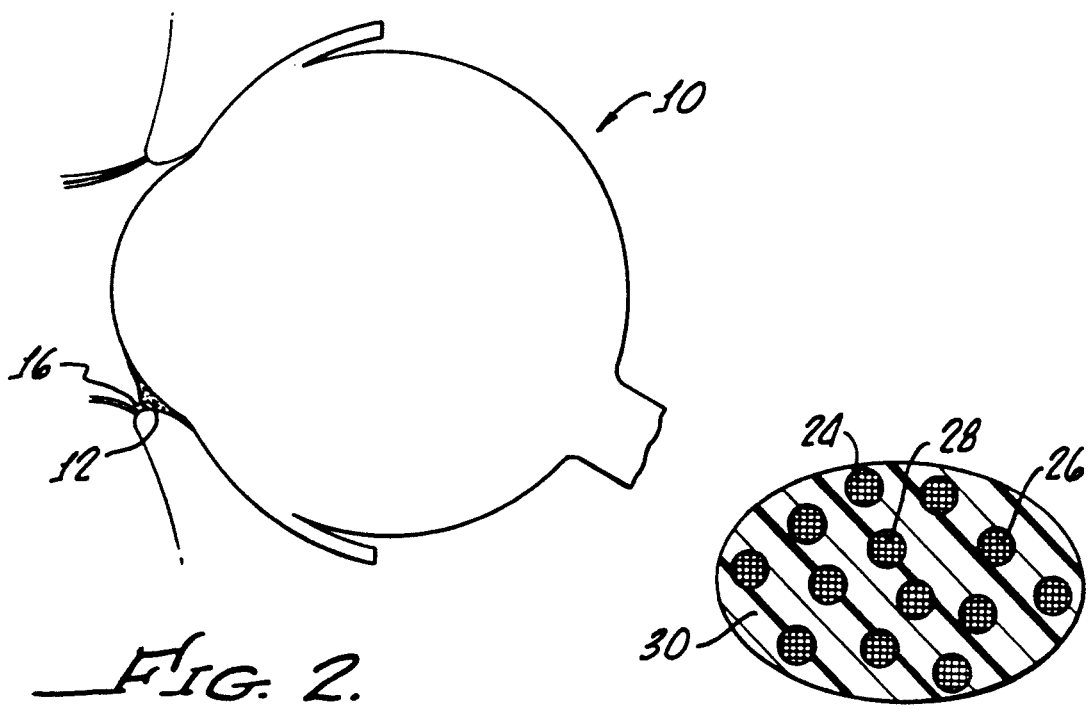
FIG. 2.
FIG. 3.

COMPOSITIONS FOR CONTROLLED DELIVERY OF PHARMACEUTICAL COMPOUNDS

FIELD OF THE INVENTION

The present invention relates in general to sustained release pharmaceutical compound delivery systems. More particularly, the present invention is directed toward pharmaceutical drug delivery compositions having improved delivery characteristics and enhanced long-term storage stability, particularly when used in conjunction with hydrophilic pharmaceutical compounds. The compositions of the present invention utilize reversibly gelling polymeric suspensions of ion exchange resin particles which have been loaded with one or more releasably bound pharmaceutical compounds.

BACKGROUND OF THE INVENTION

A common problem with the administration of many pharmaceutical compounds, including therapeutic and diagnostic drugs, has been the need to retain effective quantities of these compounds in contact with targeted tissue sites for sufficient periods of time to accomplish the desired therapeutic or diagnostic purpose. This problem is particularly acute in connection with physiological systems characterized by rapid fluid turnover or drainage. For example, in the ocular environment tear turnover and drainage through the lacrimal drainage system quickly remove the major portion of any pharmaceutical compound administered to the surface of the eye so that only a small fraction of the original dosage remains in contact with the ocular tissue for any period of time. Analogous problems are encountered in connection with the treatment of the nasal mucosa, oral and anal cavities, uro-genital track, vagina and similar physiologic environments.

Early approaches at addressing this problem generally relied upon the repeated administration of relatively large dosages of pharmaceutical compounds to compensate for the rapid loss of the compounds following their administration to the target site. Though relatively successful at maintaining effective concentrations of the desired pharmaceutical agents in contact with the target tissue such strategies were wasteful and had a number of drawbacks. These drawbacks included the expense associated with using relatively large quantities of pharmaceutical compounds, patient discomfort with repeated drug administration and systemic side-effects associated with large and frequent drug doses.

Alternative approaches to the solution of this problem utilized viscous ointments and gels as delivery vehicles for the pharmaceutical compounds. These semisolid delivery vehicles slowed down the rapid loss of the pharmaceutical compounds and retained an adequate dosage in contact with the target tissue. However, effectively delivering a controlled drug dosage with such widely variable systems proved difficult. Additionally, though satisfactory for direct topical application to mucous membranes, skin and the conjunctiva of the eye, such viscous delivery vehicles were not suitable for injection. Moreover, when utilized to treat ocular conditions such drug containing ointments and gels formed barriers to sight and produced an uncomfortable and aesthetically unpleasant crusting along the edges of the eyelids. These drawbacks as well as the possibility of blockage of the lacrimal duct when used to treat the eye lead to decreased patient acceptability and utilization of these systems.

A more modern approach directed at overcoming these problems has been the use of controlled or sustained release drug delivery systems. Typically, these systems utilize a polymeric matrix incorporating a therapeutic or diagnostic pharmaceutical compound. The polymer matrix is placed in contact with the target tissue site. Once in position, the incorporated pharmaceutical compounds are released in a controlled manner through diffusion from the polymer matrix or in response to erosion of the polymer through mechanical or chemical means. Though generally effective, a significant disadvantage associated with such macroscopic controlled release inserts was the need for medical personnel to position and remove the devices. Additionally, patient discomfort with the inserted devices limited their use.

The subsequent development of microparticulate polymeric drug delivery vehicles addressed some of these problems. Once suspended in solutions of appropriate viscosities they were capable of either topical administration or administration through injection. Additionally, when properly formulated, patients were able to self-administer such microparticulate suspensions in the form of drops or ointments. However, in spite of these successes significant problems remain with the administration and handling of microparticulate drug delivery vehicles. For example, fluid turnover or drainage at the target site may prematurely sweep the microparticulates from the target tissue along with the carrier liquid. This problem is particularly acute when microparticulate suspensions are administered as eye drops.

Further detracting from their utility, microparticulate drug delivery vehicles formed from water labile polymers must be stored in an anhydrous environment until just prior to use. Unless a liquid carrier other than water is used to suspend such microparticulates, the end user must suffer the inconvenience of combining the aqueous liquid carrier with the microparticulates immediately prior to administration. Though water labile erodible polymer microparticulates may be preferred because they do not require removal from the target site following administration, their inability to remain suspended in a ready-to-use formulation makes it virtually impossible to provide a pre-mixed water labile microparticulate drug delivery vehicle with even a minute shelf life.

Further compounding these problems, the therapeutic and diagnostic compounds that typically would be incorporated into such microparticulate delivery vehicles are often hydrophilic, water soluble, or they unfavorably interact with the polymeric matrix in the formulation. As a result, during storage in aqueous suspension these pharmaceutical compounds will leach from the microparticulate carriers into the carrier solution. This may result in a substantial loss of the desired pharmaceutical activity as well as directly impacting the ability to control the drug delivery rate from the suspension. Thus, depending upon the diffusion rate of the hydrophilic, water soluble pharmaceutical compound involved, the available shelf life of a microparticulate suspension will be much shorter than even the minimum desirable shelf life.

In addition to the problems of shelf life and long-term storage instability, when hydrophilic and water soluble pharmaceutical compounds are incorporated into polymeric drug delivery vehicles there is a significant problem in maintaining control of the actual drug delivery characteristics including drug release rate and drug delivery duration. Undesirably fast delivery rates can result from a variety of factors including the extent of drug loading within the polymer matrix, polymer swelling, diffusion rate and erosion rate as well as the length of time the polymer has remained in suspension prior to administration at the target site. Premature delivery also decreases the duration of drug availability.

An analogous drug delivery suspension directed at reducing patient discomfort associated with the administration of effective amounts of ocular pharmaceutical compounds is disclosed in U.S. Pat. No. 4,911,920 issued to Jani et al. Jani et al disclose a sustained release ophthalmic formulation for treating glaucoma without the unpleasant stinging sensation normally associated with compounds for lowering intraocular pressure. The disclosed formulation incorporates an active pharmaceutical compound held in suspension by controlled cationic-anionic interactions achieved with a cationic exchange resin dispersed in an aqueous solution or gel of a polymer. The formulation is compounded by dispersing the cationic exchange resin in water, adding the active component and then the polymer. When administered to the eye as a pourable liquid salt the active ingredient held by the cationic exchange resin and the polymer is released when the ions naturally present in the tear fluid compete with the bound active ingredient for sites on the polymer vehicle and ionic exchange resin.

While reportedly effective at reducing ocular discomfort, this formulation frequently does not have the retention capabilities of gels, cremes, and other highly viscous drug delivery formulations. The drug loaded ion exchange resin suspensions are deliverable to ocular environments utilizing drop instillable techniques, however, the suspension are subject to drainage through the lacrimal system as a result of continuous fluid turnover in the eye. Thus, while providing a medium for controlled drug delivery by way of the ion exchange resins, use of these suspension systems can result in significant and premature drug loss.

Accordingly, it is a principal object of the present invention to provide a sustained release pharmaceutical drug delivery composition having improved delivery characteristics and enhanced long-term storage stability.

It is an additional object of the present invention to provide a pharmaceutical drug delivery composition that is particularly well suited for use with hydrophilic, water soluble or water reactive pharmaceutical compounds and which can be stored for a significant period of time prior to use.

It is a further object of the present invention to provide a sustained release pharmaceutical drug delivery composition with bioadhesive properties which enhance its retention at the target site.

It is an additional object of the present invention to provide a drop instillable sustained release pharmaceutical drug delivery composition which increases in viscosity when exposed to physiological fluids thus enhancing its retention at the target site.

SUMMARY OF THE INVENTION

Generally stated, the present invention accomplishes the above-described and other objectives by providing pharmaceutical drug delivery compositions incorporating pharmaceutical compounds which are shielded from the polymeric solutions utilized to deliver the compounds. As a result these formulations provide improved delivery characteristics, formulation stability and enhanced shelf life. The compositions are particularly well suited to the administration of hydrophilic, water soluble or reactive pharmaceutical compounds when formulated in aqueous based delivery systems.

The compositions of the present invention are formulated as drug loaded, porous ion exchange resin particles incorporated in an aqueous polymeric solution. The pharmaceutical compounds are ionically bound to ionic exchange functionalities within the pores of the ion exchange resin particles prior to incorporating the ion exchange resin particles in the polymeric solution. As a result the bound drug is also shielded or locked in the pores of the ion exchange resin particles and is prevented from interacting with the polymeric solution during storage. This condition persists as long as the polymeric solution is free from salt ions or other organic ions which are small enough or sufficiently mobile to diffuse into the pores of the ion exchange resin particles. As a result, unlike many known drug delivery vehicles, the delivery compositions of the present invention remain stable during storage for significant periods of time.

The polymeric solutions incorporating the drug loaded ion exchange particles are reversibly gelling aqueous solutions having viscosities which vary in response to changes in solution pH and/or temperature. Preferred polymeric solutions exhibit relatively low viscosities at pHs below about 4 and at room temperature. When exposed to physiological temperatures and/or pH, the polymeric solutions gel to more viscous solutions. Accordingly, the pharmaceutical compound delivery compositions of the present invention can be formulated to flow freely so that they are drop instillable, yet once the compositions are administered to a targeted tissue site, the polymeric solution becomes sufficiently viscous to prolong the residency time of the drug loaded ion exchange resin particles.

Additionally, when the delivery compositions of the present invention are administered to a targeted tissue site, physiological fluids gradually co-mix with the viscous polymeric solutions. Simultaneously, small, mobile salt ions available in the physiological fluids come into contact with the drug loaded ion exchange particles. As a result, the pharmaceutical compounds bound to the incorporated ion exchange resin particles are released from the resin particles through exchange with the salt ions present in the surrounding physiological fluids in a gradual manner rather than spontaneously dumping an inappropriately large dosage. As those skilled in the art will appreciate, the unique ability of the delivery compositions of the present invention to lock pharmaceutical compounds inside the pores of ion exchange resin particles makes the delivery compositions particularly well suited for administering hydrophilic, water soluble or water reactive compounds. Thus, these pharmaceutical compounds can be formulated into aqueous polymeric solutions having a practical shelf life and desirable delivery characteristics without modifying the solubility of the pharmaceutical compounds themselves.

As mentioned above, the polymeric solutions incorporating the drug loaded ion exchange resin particles are formed from water and one or more water soluble pH-sensitive gelling polymers, and/or temperature-sensitive gelling polymers. Preferably, the gelling polymer or polymers are also bioadhesive so that once delivered to the targeted tissue site, the delivery composition will adhere to the tissue and resist being swept away by fluid turnover. Thus, delivery compositions produced in accordance with the teachings of the present invention are particularly well suited for administering pharmaceutical or diagnostic compounds through injection or as drops.

Further objects, features and advantages of the sustained release pharmaceutical compound delivery compositions of the present invention, as well as a better understanding thereof, will be afforded to those skilled in the art from a consideration of the following detailed explanation of preferred exemplary embodiments and drawings thereof.

BRIEF DESCRIPTION OF THE DRAWINGS

FIG. 1 is a sectional view of an eye illustrating the administration of an exemplary drop-instillable drug delivery composition of the present invention.

FIG. 2 is a sectional view of an eye illustrating the drug delivery composition of the present invention residing in the cul-de-sac of the eye following gelation.

FIG. 3 is an enlarged sectional view of the drug delivery composition of the present invention illustrating additional features thereof.

DETAILED DESCRIPTION OF EXEMPLARY EMBODIMENTS

The sustained release pharmaceutical compound delivery compositions of the present invention are intended for use in delivering pharmaceutical compounds to biological tissues and physiological systems, particularly those characterized by fluid turnover or drainage. Exemplary target sites include the conjunctival surface of the eye, the nasal mucosa, oral and anal cavities, uro-genital track, vagina and similar physiological environments.

In addition to effectively delivering and maintaining an appropriate dosage of therapeutic or diagnostic pharmaceutical compounds to the targeted tissue, the delivery compositions of the present invention are also configured to address a more practical problem, namely long-term storage stability and a practical shelf life for multidose drug delivery formulations.

The delivery compounds of the present invention are aqueous compositions, which are well suited for administration through injection or as drop instillable liquids or liquid sprays. In the past, such liquid suspensions of pharmaceutical compounds exhibited an undesirable degree of instability. This instability required the use of exotic solvents or two component formulations which were mixed immediately prior to administration to prevent premature leaching of the pharmaceutical compounds into solution or inactivation of the pharmaceutical compounds through interaction with solvent molecules.

Unlike the prior art drug delivery systems, the aqueous compositions of the present invention remain stable over long periods of time when formulated in multiple dose configurations. This results in a practical, shelf life which cannot be obtained with comparable prior art delivery systems. The capacity to be formulated as a stable multi-dose configuration also imparts an added degree of "ease of use" which encourages the self administration of the compounds of the present invention. What is more, the sustained release pharmaceutical compound delivery compositions of the present invention exhibit this enhanced long-term storage stability in conjunction with improved drug delivery characteristics.

This combination of properties is achieved without modifying the therapeutic or diagnostic compounds to be delivered by the compositions. Rather, the pharmaceutical compounds are locked within the pores of porous ion exchange resin particles. Then the loaded porous ion exchange resin particles are incorporated in an aqueous solution of reversibly gelling polymer.

More specifically, an exemplary sustained release pharmaceutical compound delivery composition of the present invention includes a plurality of porous ion exchange resin particles incorporated in an aqueous solution of a reversible viscosity modifying effective concentration of reversibly gelling polymer. A pharmaceutical compound or compounds are ionically and reversibly bound within the pores of the porous ion exchange resin particles with the pores being sufficiently small in size to prevent the reversibly gelling polymer from diffusing into the pores. Because of this configuration the polymer or polymers in the polymeric solution will not interact with the ionically bound pharmaceutical compound and prematurely cause the pharmaceutical compound to release into the aqueous polymeric solution.

As will be appreciated by those skilled in the art, ion exchange resins suitable for use in the present invention are widely available from a variety of commercial sources for a broad range of applications. The commercial suppliers include Bio Rad, Dow Chemical, and Rohm and Haas. Though the properties of specific ion exchange resins may vary depending upon the intended application, ion exchange resins generally consist of an insoluble porous polymer lattice or matrix with attached ionic functional groups. The variable properties include matrix structure, chemical type, functional group, degree of crosslinkage, ionic form, particle size and pore size. Exemplary commercially available ion exchange resins particularly well suited for practicing the present invention include crosslinked styrene-divinylbenzene lattice resins with either cationic or anionic functional groups.

Commercial forms of ion exchange resins are provided with counterions such as $Na^+$,$Cl^-$ and $H^+$ which are replaced by ionic forms of the desired pharmaceutical compounds. As a result, the pharmaceutical compounds are ionically bound to the ionic functional groups of the exchange resin particles. This reversible binding is readily accomplished by mixing the pharmaceutical compounds of interest with the appropriate ion exchange resin particles in a suitable solvent, for example water, as is known in the art and as will be discussed in detail below. However, broadly speaking, when the therapeutic or diagnostic pharmaceutical compound to be loaded on the porous ion exchange resin particle is basic or cationic in form, the exchange resin must be acidic. Preferably, for purposes of formulating dosage forms at optimum pH, the porous ion exchange resin is strongly acidic. For example, a suitable strong acidic ion exchange resin will contain sulfonic acid functional groups.

Conversely, when the pharmaceutical compounds of interest are acidic or anionic, the exchange resin must be basic. Depending upon the strength of the ion exchange resin, the pharmaceutical compounds of interest will be either weakly or strongly bound as desired. Additionally, it is also contemplated as being within the scope of the present invention to utilize ion exchange resins formed from silicas and cellulose having sulfonic acid groups or, alternatively, carboxylic acid or quaternary ammonium salts as the reactive sites.

It should be noted that as a further aspect of the present invention, the ion exchange resin particles are sized on the order of 1 μm to 100 μm in diameter and preferably size on the order of 1 μm to 50 μm in diameter. Particles within this size range can easily pass through the lacrimal drainage system, if desired, and also readily disperse in fluid suspension for drug loading purposes. They are also suitable for use in injectable forms of the compositions.

Preferably, the range of suitable pore sizes present in the ion exchange resin particles will vary depending upon the size of the desired pharmaceutical compound to be ionically bound within the pore as well as with the size of the reversibly gelling polymer in mind. Thus, the pore size of the resin particle lattice should be sufficiently large to bind molecules of the size of the pharmaceutical compounds of choice. Conversely, the pore size should be sufficiently small to prevent the larger aqueous polymer molecules from diffusing into the pores and possibly irreversibly reacting with the pharmaceutical compounds. As will be discussed in more detail below, many of the reversibly gelling polymers which have utility in the practice of the present invention are ionic polymers such as polycarboxylates. In aqueous solution, the mobility of these polymers is restricted by their size. Therefore, sufficiently small ion exchange resin pore sizes prevent these ionic polymers from entering the resin pores. This prohibits the polymers from ionically exchanging with the bound pharmaceutical compounds. Small pore sizes also prevent bound pharmaceutical compounds which may complex or react with the aqueous polymers from interacting with the polymers and becoming less efficacious.

Additionally, as known in the art, the size of the pores and the number of pores are directly related to the number of reactive ionic sites on the ion exchange resin particles. This will affect the amount of pharmaceutical compound which can be reversibly bound or loaded to the individual resin particles. With this in mind, exemplary pore sizes for practicing the present invention range from approximately 10 angstroms to approximately 100 angstroms.

As noted above, for purposes of delivering basic pharmaceutical compounds (such as the many drugs which are available in the hydrochloride form and which can be easily converted to the basic form) a cationic exchange resin is utilized. In particular, a sulfonic acid exchange functionality ion exchange resin such as Bio Rad AG50W-X8 is preferred. This exemplary exchange resin provides good intermediate binding capabilities with pore sizes and particle sizes within the previously noted ranges which permit the pharmaceutical compounds of choice to easily bind while preventing the polymers in solution from entering the pores and displacing or interacting with the bound pharmaceutical compounds.

The reversibly gelling polymer component utilized in the delivery compositions of the present invention are preferably aqueous solutions of physiologically compatible pH-sensitive gelling polymers, temperature-sensitive gelling polymers ionic strength sensitive gelling polymers or combinations of these polymers. As mentioned above, solutions of these polymers reversibly decrease or increase in viscosity in response to changes in pH, ionic strength, and/or temperature.

Exemplary pH-sensitive gelling polymers are acidic polymers such as polycarboxylates. Particularly suitable polycarboxylates are those polymers formed by vinyl polymerization such as polyacrylic acids, polymethacrylic acids, polymethylcrotonic acids, carboxypolymethylene, and poly(alkylvinylether/maleic acids). Aqueous solutions of these polymers can be prepared which have relatively low viscosities and flow freely within pH ranges of about 2.5 to 4.0. When the pH is raised to a typical physiological pH, such as 7.4, the solution viscosity increases until it resembles a gel. Typical viscosity modifying effective concentrations of such pH-sensitive gelling polymers range from about 0.01 wt% to 10 wt% depending upon the particular polycarboxylate and the desired range of viscosities changes.

Thermally-sensitive gelling polymers which are suitable for practicing the present invention can be selected from the group including alkyl celluloses, hydroxyalkyl celluloses, cellulosic ethers, Pluronic ® polymers and Tetronic ® polymers, with methylcellulose being particularly preferred. In a manner similar to that described above for pH-sensitive gelling polymers, aqueous solutions of thermally-sensitive gelling polymers can be formulated to have a relatively small viscosity at room temperature so that they flow easily. When the solutions are exposed to a physiological environment having an elevated temperature, for example around 35° C., the solution viscosity increases until it resembles a gel. Typical viscosity modifying effective concentrations of thermally-sensitive gelling polymers useful in the practice of the present invention are between about 0.1 wt% and 20 wt%.

As mentioned above, the aqueous polymeric solutions utilized in the delivery compositions of the present invention can include ionic polymers which, if capable of diffusing into the pores of the ion exchange resin particles, may prematurely interact or irreversibly react with the ionically bound pharmaceutical compounds. However, in accordance with the teachings of the present invention, by utilizing reversibly gelling polymers having a sufficiently high weight and in combination with a sufficiently small ion exchange resin pore size, potential interactions between polymers and bound pharmaceutical compounds are reduced to a minimum.

Accordingly, the reversibly gelling polymers utilized in the practice of the present invention will have exemplary minimum molecular weights of about 5,000. These minimum molecular weights can vary depending upon the type of polymer and the amount of volume the polymer molecule uses in solution as well as with the selected ion exchange resin pore sizes.

The drug delivery compositions of the present invention may be utilized to deliver virtually any pharmaceutical compound capable of binding to an ion exchange resin. Suitable compounds include both basic and acidic pharmaceutical. For example, a variety of pharmaceutical compounds including antibacterials, antihistaminics, antiinflammatories, miotics, anticholinergics, mydriatics, antiglaucoma compounds, antiparasitic compounds, antivirals, carbonic anhydrase inhibitors, antifungal agents, anesthetic agents, diagnostic agents, or immunosuppressive agents may be bound to the ion exchange resin particles. Specific exemplary pharmaceutical compounds include dipivalyl epinephrine, levobunolol, ofloxacin, 5-bromo-6-(imidazolin-2-ylamino)quinoxaline, clonidine, pilocarpine, flurbiprofen, timolol, betaxolol, ibuprofen, acetaminophen, and their appropriate salt forms. However, it should be emphasized that these compounds are exemplary only and are not intended to limit the scope of the present invention.

It should also be appreciated that the present invention is not limited to delivering individual pharmaceutical compounds. Combinations of pharmaceutical compounds bound to the appropriate ion exchange resins are contemplated as being within the scope of the present invention. Additionally, all resin particles need not be loaded to the same degree in order to practice the present invention. Thus, a variety of drug combinations, and drug concentrations having resultant varying release rates may be incorporated into the drug delivery compositions of the present invention. Exemplary drug loading concentrations will range from approximately 2% to 70% by weight of the resin particles.

It should be emphasized that while not essential to the practice of the present invention, bioadhesiveness is a particularly advantageous property of the exemplary polymeric materials described. Utilizing a solution of a bioadhesive polymer to incorporate the loaded ion exchange resin particles gives the delivery composition the ability to adhere to biological tissue following administration. This adhesive action ensures that the drug delivery composition is retained at the target site in a safe and non-irritating manner. Additionally, this makes the delivery compositions of the present invention particularly well suited for delivering ophthalmic pharmaceutical to the ocular environment as they resist lacrimal drainage without interfering with vision.

A preferred alternative aqueous solution of reversibly gelling polymer includes both a pH-sensitive gelling polymer and thermally-sensitive gelling polymer. Since delivering the compositions of the present invention to a target tissue site can involve changes in both temperature and pH, such a solution will respond with a viscosity increase in response to both a temperature change and pH change. Furthermore, the solution gelling behavior of such polymers is synergistic which necessarily results in lower viscosity modifying effective concentrations. Preferably, the exemplary alternative aqueous solutions utilized in the present invention are approximately 3 wt% methylcellulose and approximately 0.9 wt% carboxypolymethylene.

Preparing the sustained release pharmaceutical compound delivery compositions of the present invention is relatively straight forward. Generally the compositions are formed by first providing a plurality of ion exchange resin particles having pores and ionic functionalities within the pores as discussed above. Next, the pores of the plurality of ion exchange resin particles are loaded with at least one pharmaceutical compound of choice. Finally, the loaded ion exchange resin particles are incorporated in an aqueous solution of a reversible viscosity modifying effective concentration of suitable polymer.

As described above, commercial ion exchange resin particles are readily available in a wide variety of sizes, ionic functionalities, and materials. Preferably, the ion exchange resin particles have pore sizes between about 10 angstroms and about 100 angstroms and the particle diameter is between about 1 μm and about 100 μm and preferably between about 1 μm and 50 μm. Particularly suitable ion exchange resin particles are crosslinked polystyrene-divinylbenzene resins. When the delivery compositions of the present invention are utilized to deliver the more prevalent basic pharmaceutical compounds, sulfonic acid exchange functionalities are preferred. However, in situations for which acidic compounds are selected for delivery, quaternary ammonium functionalities are preferred.

Loading the pores of the ion exchange resin particles with at least one pharmaceutical compound is accomplished by providing a concentrated liquid solution, preferably aqueous of the pharmaceutical compounds of interest. Simple mixing of the ion exchange resin particles with the liquid solution will cause the pharmaceutical compound in the solution to exchange with the ions on the resin and to ionically bind to the resin particles. In cases in which the ion exchange resin is in the hydrogen form, the pH of the aqueous solution should be carefully adjusted to maintain a pH balance as the hydrogen ion exchanges with the pharmaceutical compound. Finally, the loaded ion exchange resin particles are removed from the liquid solution. Depending upon the size of the pharmaceutical compound and the pore size of the ion exchange resin particles (which determines the resin loading capacity) the loaded ion exchange resin particles will incorporate from about 2 wt% to about 70 wt% pharmaceutical compound.

Once the ion exchange resin particles have been loaded with the releasably and ionically bound pharmaceutical compound or compounds of choice and removed from the liquid loading solution they are incorporated into an aqueous solution of reversibly gelling polymer by simply mixing the desired amount of loaded ion exchange resin particles with an aqueous solution of the polymer of choice. It should be noted that prior to mixing the loaded particles with the aqueous solution of reversibly gelling polymer, it may be desirable to adjust the pH of the polymer solution. As described above, this aids in maintaining a low pH and a low solution viscosity when certain polycarboxylate polymers are utilized.

Once formulated in accordance with the teachings of the present invention, the pharmaceutical compound or compounds or choice are locked within the pores of the ion exchange resin particles and the presence of even charged polymers in the aqueous solution will not cause the pharmaceutical compounds to prematurely exchange and migrate into solution. Additionally, pharmaceutical compounds which complex or otherwise are unstable in the presence of charged polymers such as the carboxypolymethylenes can be effectively utilized suspended in such compositions for extended periods of time once sequestered within the appropriately sized porous exchange matrix. As a result, the compositions of the present invention can be stored for long periods of time without degradation. Because the compositions have stable long-term storage characteristics, they can be prepared, stored and finally administered to a tissue site without additional handling by the patient. As a result, ready-to-use multiple packaging can be employed effectively when preparing and administering these drug delivery vehicles through a variety of administration routes such as injection or a dropable liquid or sprays.

For example, while the drug delivery compositions of the present invention are useful for administering drugs to a variety of tissue sites, they are particularly suitable for delivering drugs to the ocular environment, a process which is generally illustrated in FIGS. 1-3. More specifically, FIG. 1 illustrates a vertical section view of an eye 10 having a lower cul-de-sac 16 formed by the conjunctiva 20 and the lower eyelid 22. The eye 10 of FIG. 1 is receiving a low viscosity liquid drop 12 of the drug delivery composition of the present invention from an eye dropper type device 14. Following administration to the ocular environment the liquid drop rapidly gels to a viscous, bioadhesive form as shown in FIG. 3, an enlarged view of the delivery composition illustrating the porous ion exchange resin particles, represented by numerals 24, 26, and 28 entrapped in the reversibly gelling polymer 30. As shown in FIG. 2, following gelation the drop 12 remains in its delivered position within the lower cul-de-sac 16 of eye 10 with a minimum of patient discomfort.

Once delivered to the targeted tissue site, the polymeric solutions used in the drug delivery compositions of the present invention immediately increase in viscosity. Depending upon the selected reversible gelling polymer in the composition solution, the increase in viscosity is triggered by the increase in solution temperature from ambient to physiological temperatures and/or changes in solution pH to the pH of physiological fluids or the solution ionic strength. Concurrently, with this increase in viscosity, the salt ions in the physiological fluids begin to migrate into the polymeric solution, whereby they come into contact with the pharmaceutical compound loaded ion exchange resin particles. When the ionic activity within the vicinity of the ion exchange resin particles becomes sufficiently high, the ionically bound pharmaceutical compound exchanges with the salt ions. This exchange is a gradual displacement process which results in a controlled sustained release of the loaded pharmaceutical compounds. Moreover as the pharmaceutical compound gradually dissociated the resin particles, the water soluble polymer of the polymeric solution begins to dissolve in the surrounding physiological fluids. This erosion process slowly exposes the released pharmaceutical compound to the surrounding tissue making the active drug available for diagnostic or therapeutic treatment.

With this understanding in mind, the following examples are offered as being illustrative of the principles of the present invention and not by way of limitation.

EXAMPLE I

Preparation of Exemplary Sustained Release Delivery Composition 0.2 g of cationic ion-exchange resin (Bio-Rad AG50w-x8) was added to a 10 ml aqueous solution of levobunolol hydrochloride (2% w/v), and was allowed to equilibrate for 24 hours under mild stirring to load the ion exchange resin. The suspension was then filtered through 10 $\mu$m filter paper to remove the loaded resin from the solution. The levobunolol hydrochloride concentration in the residual solution had dropped to 0.2% w/v indicating that 90% of the drug originally present was bound to the resin. The loaded resin, shielded from light, was dried in a vacuum oven for six hours.

EXAMPLE II

Preparation of Alternative Pharmaceutical Compound Delivery Composition 0.1 g of cationic ion-exchange resin (Bio-Rad AG50w-x16) was added to 3 ml of an aqueous solution of pilocarpine hydrochloride (5% w/v) and allowed to equilibrate for 24 hours under mild stirring to load the resin particles. The suspension was then filtered through 1.2 $\mu$m filter paper to remove the resin from the solution. The pilocarpine hydrochloride concentration remaining in the solution had dropped to 1% w/v indicating that 80% of the drug originally present in solution was bound to the resin. The loaded resin was dried in a vacuum oven for six hours.

EXAMPLE III

Preparation of Drug-Containing Cation Exchange Resin in a Reversibly Gelling Polymer Composition Two 10 mL solutions of 5% w/v dipivalyl epinephrine hydrochloride (DPE) in deionized water were prepared. 1 g of pre-washed Rad AG50W-X16 hydrogen form resin 36–44 $\mu$m in diameter was added to one 10 mL solution (Sample A) and 1 g of pre-washed Bio-Rad AG50W-X8 hydrogen form resin 63–150 $\mu$m in diameter was added to the second 10 mL solution (Sample B). Each sample was then agitated continuously for 24 hours and the concentration of DPE in the deionized water was measured periodically during the 24-hour period. The measured DPE concentrations in Sample A and Sample B are shown in Table I.

TABLE I

| Time (hr) | Conc. of DPE in Sample A | Conc. of DPE in Sample B |
|---|---|---|
| 0 | 5.0% | 5.0% |
| 0.5 | 4.3 | 3.0 |
| 1 | 4.1 | 2.6 |
| 3 | 3.9 | 1.9 |
| 6 | 3.7 | 1.8 |
| 24 | 3.0 | 0.5 |

After 24 hours 40% of the DPE in the initial 5% w/v solution of Sample A was loaded on the AG50W-X16 resin and 90% of the DPE in the initial 5% w/v solution of Sample B was loaded on the AG50W-X8 resin. The loaded resin particles obtained from Sample A and Sample B were separately washed with deionized water 3 times and stored in a vacuum oven until they dried.

Two reversibly gelling polymer solutions of 1% w/v hydroxypropylmethylcellulose (Dow Coring, Methocel A4M) and 0.3% w/v Carbopol 940 (BF Goodrich) were prepared by heating two 50 mL portions of deionized water to 85° C. and adding 0.5 g Methocel A4M to each portion, cooling the solutions to room temperature and adding 0.15 g Carbopol 940 to each portion. A final drug delivery composition was prepared by adding 0.05 g of the loaded resin particles obtained from Sample A and Sample B to the reversibly gelling polymer solutions, respectively. The effective concentration of DPE in the composition containing Sample A was 0.04% and in the composition containing Sample B the DPE concentration was 0.08%.

EXAMPLE IV

Shelf Stability of DPE in Ion Exchange/Carbopol-Methocel Gel

Three duplicates of the drug delivery composition containing AG50W-X8 as prepared in Example III were stored at 5° C., 23°, and 37° C., respectively. After the first month of storage, no degradation of DPE was detected in any of the samples. After four months the concentration of DPE in the 37° C. sample was reduced to 58% of the original concentration. However, the concentrations of DPE in the 5° C. and 23° C. samples, respectively, remain unchanged within the experimental uncertainty ($\pm 10\%$).

In contrast, three aqueous DPE solutions which were stored at 5° C., 23° C. and 37° C. decreased in concentration by 6%, 4%, and 12%, respectively, after 1 month of storage. Following 4 months of storage at these same temperatures, the DPE had decreased in concentration by 17%, 9%, and 68% respectively.

EXAMPLE V

Release of Dipivalyl Epinephrine Hydrochloride from Cationic Ion Exchange 0.3 g portions of Sample A and Sample B prepared in Example III were dispersed in two 900 mL normal saline solutions, respectively. The dispersions were kept at room temperature with agitation for a period of 24 hours. The cumulative release of dipivalyl epinephrine from each of the two cation exchange resins is shown in Table II.

TABLE II

| Time (hr) | % Release of DPE from AG50W-X8 | % Release of DPE from AG50W-X16 |
|---|---|---|
| 0 | 0 | 0 |
| 0.5 | 22 | — |
| 1 | 30 | 12 |
| 2 | 40 | 20 |
| 4 | 53 | 34 |
| 24 | 87 | 77 |

EXAMPLE VI

Preparation, Stability, and Drug Release of Flurbiprofen Sodium/Anion Exchange Resin System A 0.2 g portion of analytical grade chloride form anionic exchange resin particles having diameters in the range 45–106 μm and available from Bio-Rad as AG2-X8 was suspended in 10 mL of a 2% w/v aqueous solution of flurbiprofen sodium. The suspension was allowed to equilibrate for 24 hours with mild agitation and the flurbiprofen sodium concentration in the aqueous medium was measured. After 24 hours 45% of the flurbiprofen sodium was loaded within the pores of the resin particles. The resin particles were washed 3 times with deionized water and dried in a vacuum oven at room temperature for 2 days. A 0.3 g portion of the loaded resin particles was dispersed in 300 mL of an aqueous normal saline solution. The dispersion was agitated at room temperature for 7 hours while the release of flurbiprofen from the resin particles was measured. The results of these measurements are illustrated in Table III.

TABLE III

| Time (hour) | % release of flurbiprofen sodium |
|---|---|
| 0 | 0 |
| 0.5 | 27% |
| 1 | 44% |
| 3 | 67% |
| 7 | 97% |

Another 0.3 g of flurbiprofen-loaded resin was prepared as described above and dispersed in deionized water and stored at 45° C. The pH of this dispersion was adjusted to 5.0 with acetic acid. The deionized water was periodically assayed for flurbiprofen concentration. The results showed that the drug remains bound to the resin particles and leakage is less than 4%. The chemical stability of the bound drug is illustrated in Table IV:

TABLE IV

| Time (week) | Concentration of Drug as % of original |
|---|---|
| 0 | 100 |
| 1 | 97.3 |

TABLE IV-continued

| Time (week) | Concentration of Drug as % of original |
|---|---|
| 3 | 96.8 |
| 4 | 97.5 |
| 6 | 96.9 |

EXAMPLE VII

Preparation of Sodium Form Ion Exchange 20 g of hydrogen form ion exchange resin particles with diameters in the range 106–250 m available as AG50W-X4 from Bio-Rad were dispersed in 200 mL of aqueous 2N NaCl. The dispersion was continually agitated for 3 hours and the pH was maintained between 7.0 and 8.0 by adding 1N NaOH as needed. After 3 hours the dispersion pH remained stable, indicating the an equilibrium concentration of sodium ion in the resin particles had been reached. The resin particles were washed and filtered 3 times using a 0.45 μm nylon filter and deionized water.

EXAMPLE VIII

Release of Levobunolol Hydrochloride from Ion Exchange 5 g each of Bio-Rad AG50W-X8 38–63 μm in diameter and AG50W-X16 53–106 μm in diameter were converted from the hydrogen form to the sodium form using the procedure described in Example VII. Levobunolol hydrochloride was loaded on the resins using the method described in Example I. The amount of levobunolol hydrochloride in each of the resins was determined to be 0.85 g levobunolol hydrochloride per gram AG50W-X8 resin and 0.32 g levobunolol hydrochloride per gram AG50W-X16 resin.

0.3 g portions of each of the two levobunolol-loaded resins were then dispersed in 900 mL of normal saline solution, respectively. The dispersions were kept at room temperature and agitated for a period of 24 hours. The cumulative release of levobunolol from the two cation exchange resin is shown in Table V.

TABLE V

| Time (hr) | % Release of Levobunolol from AG50W-X8 | % Release of Levobunolol from AG50W-X16 |
|---|---|---|
| 0 | 0 | 0 |
| 0.5 | 50 | 6 |
| 1 | 60 | 8 |
| 3 | 80 | 16 |
| 5 | — | 21 |
| 8 | — | 30 |
| 24 | 83 | 28 |

EXAMPLE IX

Shelf Stability of Levobunolol Hydrochloride in Ion Exchange Resins

Two levobunolol-containing resin samples were prepared as described in Example VIII and dispersed separately in deionized water to form sample 0.2% dispersions. Two sample dispersions and a control drug solution were stored at room temperature. Two sample dispersions and a control drug solution were also stored at 45° C. The four samples were periodically assayed for drug concentration in the deionized water. The results show that in all resin-containing samples the drug remains bound to the resin and leakage is less than 2%.

The chemical stability of the drug compared with the resin-free control is presented in Table VI:

TABLE VI

| Time (week) | Concentration Of Drug As A Percentage of Control | | | |
| --- | --- | --- | --- | --- |
| | AG50W-X8 | | AG50W-X16 | |
| | room temp | 45° C. | room temp | 45° C. |
| 0 | 100 | 100 | 100 | 100 |
| 1 | 80 | 98 | 54 | 62 |
| 2 | 90 | 118 | 100 | 90 |
| 3 | 91 | 96 | 58 | 49 |
| 4 | 87 | 88 | 50 | 62 |
| 6 | 100 | 105 | 123 | 128 |

EXAMPLE X

Release of 5-bromo-6-(imidazolin-2-ylamino)-quinoxaline Hydrochloride (BIYQ) from Ion Exchange 5 g each pf Bio-Rad AG50W-X8 38–63 μm in diameter and AG50W-X16 53–106 μm in diameter were converted from hydrogen form to sodium form using the procedure described in Example VII. BIYQ was loaded on the resins using the same method outlined in Example I. The amount of BIYQ in the two types of resins after loading was analyzed and found to be 0.96 g drug/g AG50W-X8 resin and 0.44 g drug/g AG50W-X16 resin, respectively. 0.3 g portions of each of the two BIYQ-loaded resins were then dispersed in 900 mLs of normal saline solution, respectively. The dispersions were kept at room temperature with agitation for a 24 hour period. The cumulative release of levobunolol from the two cation exchange resin is shown in Table VII.

TABLE VII

| Time (hr) | % Release of BIYQ from AG50W-X8 | % Release of BIYQ from AG50W-X16 |
| --- | --- | --- |
| 0 | 0 | 0 |
| 0.5 | 40 | 9 |
| 1 | 83 | — |
| 3 | 89 | 46 |
| 8 | — | 55 |
| 24 | 91 | 63 |

In closing, it should be understood that the embodiments of the present invention disclosed herein are illustrative of the principles of the present invention and that other modifications may be employed which are within the scope thereof. For example, drug loaded ion exchange resin particles may be formed by suspending the loaded exchange resin particles in an emulsion of the polymeric solutions. Accordingly the present invention is not limited to that precisely as disclosed and described and is limited only by the appended claims.

I claim:

1. A sustained release drop instillable pharmaceutical compound delivery composition having long-term storage stability, said composition comprising:
   a plurality of porous ion exchange resin particles sized from about 1 μm to about 50 μm in diameter, said porous ion exchange resin particles incorporated in an aqueous solution of from about 0.1 wt % to about 10 wt % methylcellulose wherein such aqueous solution has a free flowing, drop instillable viscosity at room temperature and at a pH value of from about 2.5 to 4.0, and a gel-like viscosity at a pH value of about 7.4 and at about 35° C.; and
   at least one pharmaceutical compound ionically bound within said pores of said ion exchange resin particles, said porous ion exchange resin particles having a pore size sufficiently small to prevent said methylcellulose from diffusing into said pores.

2. A sustained release drop instillable pharmaceutical compound delivery composition having long-term storage stability, said composition comprising:
   a plurality of porous ion exchange resin particles sized from about 1 μm to about 50 μm in diameter, said porous ion exchange resin particles incorporated in an aqueous solution of from about 0.1 wt % to about 10 wt % methylcellulose and from about 0.01 wt % to about 10 wt % polycarboxylate, wherein such aqueous solution has a free flowing, drop instillable viscosity at room temperature and at a pH value of from about 2.5 to 4.0, and a gel-like viscosity at a pH value of about 7.4 and at about 35° C.; and
   at least one pharmaceutical compound ionically bound within said pores of said ion exchange resin particles, said porous ion exchange resin particles having a pore size sufficiently small to prevent said methylcellulose and said polycarboxylate from diffusing into said pores.

3. A process for forming a sustained released drop instillable pharmaceutical compound delivery composition having long-term storage stability, said process comprising the steps of:
   providing a plurality of ion exchange resin particles, each of said ion exchange resin particles having pores and surface ionic functionalities within said pores;
   loading said pores of said plurality of ion exchange resin particles with at least one pharmaceutical compound; and
   incorporating said loaded plurality of ion exchange resin particles in an aqueous solution of from about 0.1 wt % to about 10 wt % methylcellulose wherein said aqueous solution has a free flowing, drop instillable viscosity at room temperature and at a pH value of from about 2.5 to 4.0, and a gel-like viscosity at about 35° C. and a pH value of about 7.4.

4. A process for forming a sustained released drop instillable pharmaceutical compound delivery composition having long-term storage stability, said process comprising the steps of:
   providing a plurality of ion exchange resin particles, each of said ion exchange resin particles having pores and surface ionic functionalities within said pores;
   loading said pores of said plurality of ion exchange resin particles with at least one pharmaceutical compound; and
   incorporating said loaded plurality of ion exchange resin particles in an aqueous solution of from about 0.1 wt % to about 10 wt % polycarboxylate and from about 0.1 wt % to about 10 wt % methylcellulose wherein said aqueous solution has a free flowing, drop instillable viscosity at room temperature and a pH value of from about 2.5 to 4.0, and a gel-like viscosity at 35° C. and a pH value of about 7.4.

* * * * *